United States Patent [19]

Badra

[11] 4,433,682

[45] Feb. 28, 1984

[54] ANKLE PROTECTOR

[76] Inventor: Sami A. Badra, 6186 College Ave., San Diego, Calif. 92101

[21] Appl. No.: 353,318

[22] Filed: Mar. 1, 1982

[51] Int. Cl.³ .................... A61F 5/30; A61F 3/00; A61F 13/06

[52] U.S. Cl. .................... 128/153; 128/80 R; 128/166

[58] Field of Search ............ 128/165, 166, DIG. 15, 128/157, 169, 80 H, 153, 80 R

[56] References Cited

U.S. PATENT DOCUMENTS

| | | | |
|---|---|---|---|
| 3,506,000 | 8/1968 | Baker | 128/DIG. 15 |
| 3,508,544 | 4/1970 | Moore et al. | 128/153 |
| 3,926,186 | 12/1975 | Nirschl | 128/165 |
| 3,942,525 | 3/1976 | Dragan | 128/DIG. 15 |
| 4,076,022 | 2/1978 | Walker | 128/153 |
| 4,186,738 | 2/1980 | Schleicher et al. | 128/80 R |

*Primary Examiner*—Henry J. Recla
*Assistant Examiner*—Karin Reichle
*Attorney, Agent, or Firm*—Ralph S. Branscomb

[57] ABSTRACT

An ankle protector is provided utilizing a planar slab of high density, flexible, soft foam material shaped to wrap around the rear of the ankle, and calf there being a heel cutaway for positioning purposes, and a pair of relatively thin, wide straps extending from the rear surface of the panel at one side, wrapping around the front of the ankle, and releasibly connecting to the rear surface of the panel at the other side, to securely position the pad behind the ankle.

1 Claim, 5 Drawing Figures

ANKLE PROTECTOR

BACKGROUND OF THE INVENTION

It is a known fact that crossing the legs, particularly at the ankle, cuts off the circulation to the feet and is a major factor in causing blood clots in the feet. For this reason, there are often signs in hospitals, at least in the rooms having television sets, suggesting that the patients not cross their legs and prop them up on the foot of the hospital bed or other hard edge, but rather keep them straight lying flat on the bed.

The position in which the legs are crossed and propped on the edge of a desk or end of a bed is a very comfortable position, except for the pressure on the lower leg at the ankle and calf. It is also a position that is very easy on the heart, inasmuch as the feet are up near the head level, and the body is basically reclined.

There is a need, therefore, for some apparatus to protect the calves and the rear ankles and permit the legs to be crossed and propped on a hard surface.

SUMMARY OF THE INVENTION

The invention meets the above stated need and comprises a protector, ordinarily provided in pairs, each of which has a planar slab of fairly high density, but very soft and pliable, foam, together with a pair of retaining straps which are preferably made of a thin, fabric-backed foam, the backing of which engages a pair of hook-and-fastener style hooks positioned on the rear surface of the planar panel.

The panel itself is shaped to best accommodate the rear of the ankle, there being a notch or cutaway portion just above the heel to assist in positioning the pad, with the upper portion extending beyond the upper most strap and being rounded, thus minimizing the effect of any sharp edge extant at the termination of the upper edge of the panel.

By positioning one of these protectors on each foot, the wearer can not only cross the legs at the ankle, rest the legs on a desk or other sharp surface or edge without feeling any pain or without having detrimental effects on the circulation, but because of the compact fitness and design of the protectors they can be worn beneath the trouser leg, unnoticed, and actually need never be taken off except when removing the trousers. Additionally of course, they may be used in hospital rooms and other places such as nursing homes and the like where recooperating or ill patients may enjoy the comforts of resting their legs in an elevated position.

DETAILED DESCRIPTION OF THE PREFERRED EMBODIMENT

Figure 1:
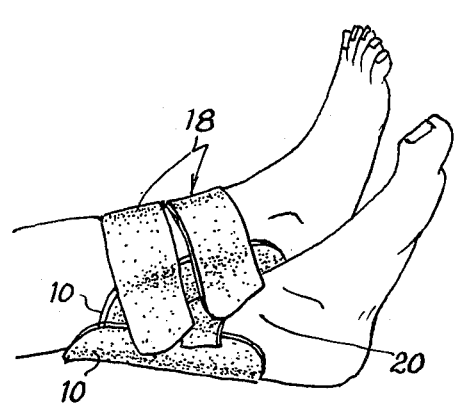
FIG. 1 is a side elevation view illustrating a pair of the protectors in use.

The unit is of basically simple construction, consisting of a planar panel 10 of fairly high density foam, being on the order of $\frac{3}{8}$ of an inch thick. In the simplest form of construction, this panel need not be backed or faced with any other fabric, as the high density foam itself defines a suitable exterior surface.

On the backside of each of the planar panels 10 are placed a pair of patches 12 having hook-type fasteners 14 of the Velcro TM variety. These hooks cooperate with the fabric facing 16 bonded to the straps 18 so that the straps may be wrapped around ankles such as at 20, with the facing fabric engaged at any position along its length on the patches 12.

The fixed ends 22 of the straps are bonded with a suitable glue to the panel, with the facing fabric lying on the side of the straps which is to be bonded, to insure a secure connection.

The straps themselves, aside from the thin layer of facing fabric which doubles as a strengthening element and fastening means, are composed of a thin foam, about $\frac{1}{8}$ of an inch thick, so that these straps also have a cushioning effect as well as a connective one. Thus, when one of the protectors is wrapped around each ankle as shown in FIGS. 1 and 2, the bottom of the ankle is very well protected due to the relatively thick foam panel 10, so that when the ankle is rested against a desk, or the other ankle, it is protected from below.

Although when the legs are crossed, the bottom panel of the top ankle would tend to protect the top of the bottom ankle, nevertheless, in case any portions of the shoe heel or other hard objects happen to be positioned against the top of the foot, these straps 18 will protect them.

Turning to the exact shape of the planar panels 10, they are basically rectangles with rounded corners, except for a cutaway notch 24 for the heel of the user. This notch comfortably fits over the heel of the foot, or over the heel of the shoe, helping to retain the padded panel in place and prevent it from sliding or creeping when in use. This is particularly important when the protectors are worn under the trouser legs throughout the day, when they might tend to rotate or jostle upwards or downwards while walking or moving about.

Figure 2:
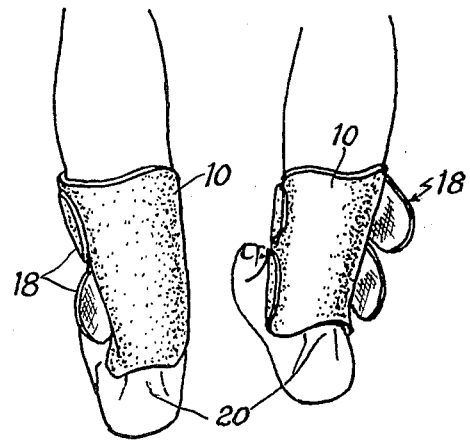
FIG. 2 is a rear elevation view of the ankles of a user with the protectors in place.
Figure 3:
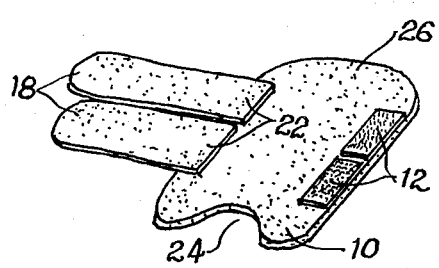
FIG. 3 is a perspective view of the left-handed version of the protector.
Figure 4:
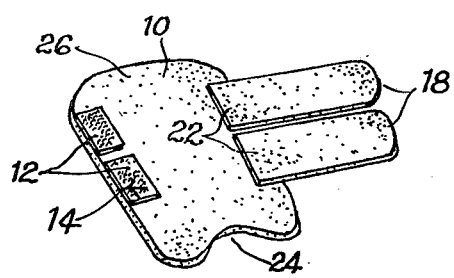
FIG. 4 is a perspective view of the right-handed version.
Figure 5:
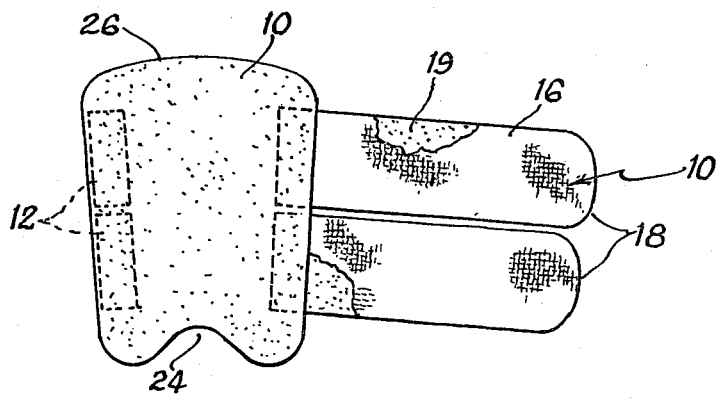
FIG. 5 is a plan view of the protector lying face down.

Because it is desirable to have the straps 18 on the outside of the ankle, rather than on the inside, as shown in FIG. 2, ideally they should be provided in right and left-hand versions, as shown in FIGS. 3 and 4, respectively. The only difference of course is that identical planar panel units are fitted on opposite sides with the hook patches and the straps.

One other feature that is worthy of mention is the fact that the top portion of the panel is a smoothly rounded curve, shown at 26. This cooperates with the level of the top edge of the top connector strap, which falls more than an inch beneath the top of the curved edge 26. Because the uppermost strap edge does not come to the very perimeter of the panel, when it is tightened around the ankle, the tension line does not coincide with the edge of the panel pad which might create a sharp line of force against the ankle. Instead, the curved portion 24 of the pad extends upwardly for a little more than an inch, so that what otherwise would be a pressure edge is instead dissipated over a wide area of the panel above strap level.

The instant invention, as indicated above, can be used both under the trouser leg throughout the day, as well as at home when watching television or lying in a hospital bed. Because of its compactness, its universal adjustability, and its simplicity of manufacture, it will undoubtably provide a welcome relief to those who have suffered from sore ankles caused by crossing the ankles, and those who have circulation problems and thus do not enjoy the benefits of crossing the legs.

While the preferred embodiment of the invention has been described, other modifications may be made thereto and other embodiments may be devised within the spirit of the invention and scope of the appended claims.

What is claimed is:

1. A pair of ankle and calf protectors, each comprising:
   (a) a planar panel of resilient foam material having front and rear surfaces and top and bottom edges and being shaped to wrap around the rear of the ankle and lower calf, and having a concave cut-away portion defined in its bottom edge to fit the heel of the user;
   (b) said panel having a lateral dimension sufficient to wrap around a portion of the ankle and lower calf and being sufficiently small to wrap around a small ankle without overlapping onto itself;
   (c) strap means for securing said panel around an ankle, said strap means being secured at one end to the rear surface of said panel and the other end being removably securable at adjustable positions to the rear surface of said panel, whereby said panel can be applied against the rear of the ankle with said strap means wrapped around the front of the ankle and secured to the rear surface of the panel,
   (d) said strap means comprises two bands of wide, parallel closely adjacent straps of resilient foam material to substantially cover the front of the ankle and calf over an area on the order of at least three-fourths of the height of said panel to protect the front of the ankle and calf as well as hold said panel in place;
   (e) said foam straps being faced with a bonded fabric and said panel defining a hook-type fasteners on the rear surface thereto to engage said fabric at selectable portions along the lengths of said straps and retain said panel snugly on the ankle due to the resilient nature of the straps; and
   (f) each of the protectors of said pair having said hook-type fasteners and straps on the opposite side of said panel from the other of the said protectors such that such pair defines left and right-hand protectors with ends of the straps being wearable on the outer side of each leg to prevent brushing against the straps of the other protector of said pair.

* * * * *